US005824213A

United States Patent [19]
Utterberg

[11] Patent Number: 5,824,213
[45] Date of Patent: Oct. 20, 1998

[54] SEPARABLE HEMODIALYSIS SYSTEM

[75] Inventor: David S. Utterberg, Seattle, Wash.

[73] Assignee: Medisystems Technology Corporation, Las Vegas, Nev.

[21] Appl. No.: 937,121

[22] Filed: Sep. 24, 1997

Related U.S. Application Data

[63] Continuation of Ser. No. 301,765, Sep. 7, 1994, abandoned.

[51] Int. Cl.$^6$ ............................ B01D 61/28; B01D 61/30
[52] U.S. Cl. ........................ 210/241; 210/134; 210/143; 210/195.2; 210/646; 210/929
[58] Field of Search .................................. 210/134, 143, 210/241, 195.2, 321.71, 646, 929; 604/4, 5, 6; D24/186, 216, 107

[56] References Cited

U.S. PATENT DOCUMENTS

| | | | |
|---|---|---|---|
| 3,774,762 | 11/1973 | Lichtenstein | 210/929 |
| 3,946,731 | 3/1976 | Lichtenstein | 210/929 |
| 4,083,777 | 4/1978 | Hutchisson | 210/646 |
| 4,293,413 | 10/1981 | Schnell | 210/188 |
| 4,324,662 | 4/1982 | Schnell | 210/646 |
| 4,353,368 | 10/1982 | Slovák et al. | 210/646 |
| 4,897,184 | 1/1990 | Shouldice et al. | 210/87 |
| 5,211,849 | 5/1993 | Kitaevich et al. | 210/645 |
| 5,326,476 | 7/1994 | Grogan et al. | 210/646 |
| 5,372,709 | 12/1994 | Hood | 210/929 |
| 5,520,640 | 5/1996 | Utterberg | 604/80 |

FOREIGN PATENT DOCUMENTS

| | | |
|---|---|---|
| 568275 | 11/1993 | European Pat. Off. . |
| 1521260 | 5/1967 | France . |
| 1 566 662 | 8/1967 | Germany . |
| 3426493 | 7/1984 | Germany . |
| PCT/US80/ 00952 | 7/1980 | WIPO . |
| 9211878 | 7/1992 | WIPO . |

OTHER PUBLICATIONS

Polish Tech. Rev., vol. 113, No. 1, p. 19 (1979).
AK–10 System, Operator's manual for hemofiltration BMM 10–1 HFM 10–1, Gambro AB, Lund, Sweden (1986).
*Portable Artificial Kidney Systems* brochure, Junken Co., LTD, Japan (undated).
*Dialysate Preparation Unit*, Therapeutic Systems by SIS.TER, Italy (undated).
*Blutmonitor BM 11* brochure, Dialyse Technik, Germany (undated).
*Monitral S*, User Friedly Technology brochure, Hospal Technology, USA (undated).
*BSM 21—BSM 22 blood safety modules*, Hospal brochure, Hospal Technology, USA (undated).
*Holger Crafoord and Anders Althin* brochure, Gambro, Sweden (undated).

*Primary Examiner*—John Kim
*Attorney, Agent, or Firm*—Gerstman, Ellis & McMillin, Ltd.

[57] ABSTRACT

A hemodialysis system comprises the following: a dialysate handling unit for providing dialysate to the patient. This unit comprises a hemodialysis solution pump and apparatus for monitoring hemodialysis solution safety such as a conductivity tester. Additionally a solution heater and appropriate conventional controls can be provided, as well as a proportioning system, an ultrafiltration measuring unit, and other known apparatus for handling dialysis solution. A blood handling unit is also provided, which comprises a membrane dialyzer and holder, a blood pump, blood flow tubing and safety equipment for monitoring blood flow as it is pumped through the arterial/venous blood conduit set tubing from the patient, through the membrane dialyzer, and back to the patient. A first conduit is present for conveying fresh dialysate from the dialysate handling unit to the blood handling unit (or directly to the membrane dialyzer). A second conduit is provided for conveying spent hemodialysis solution away from the blood handling unit. By this invention, the dialysate handling unit and the blood handling unit are separate from and movable relative to each other while the hemodialysis is being performed. Significant economic and functional advantages can be achieved.

27 Claims, 2 Drawing Sheets

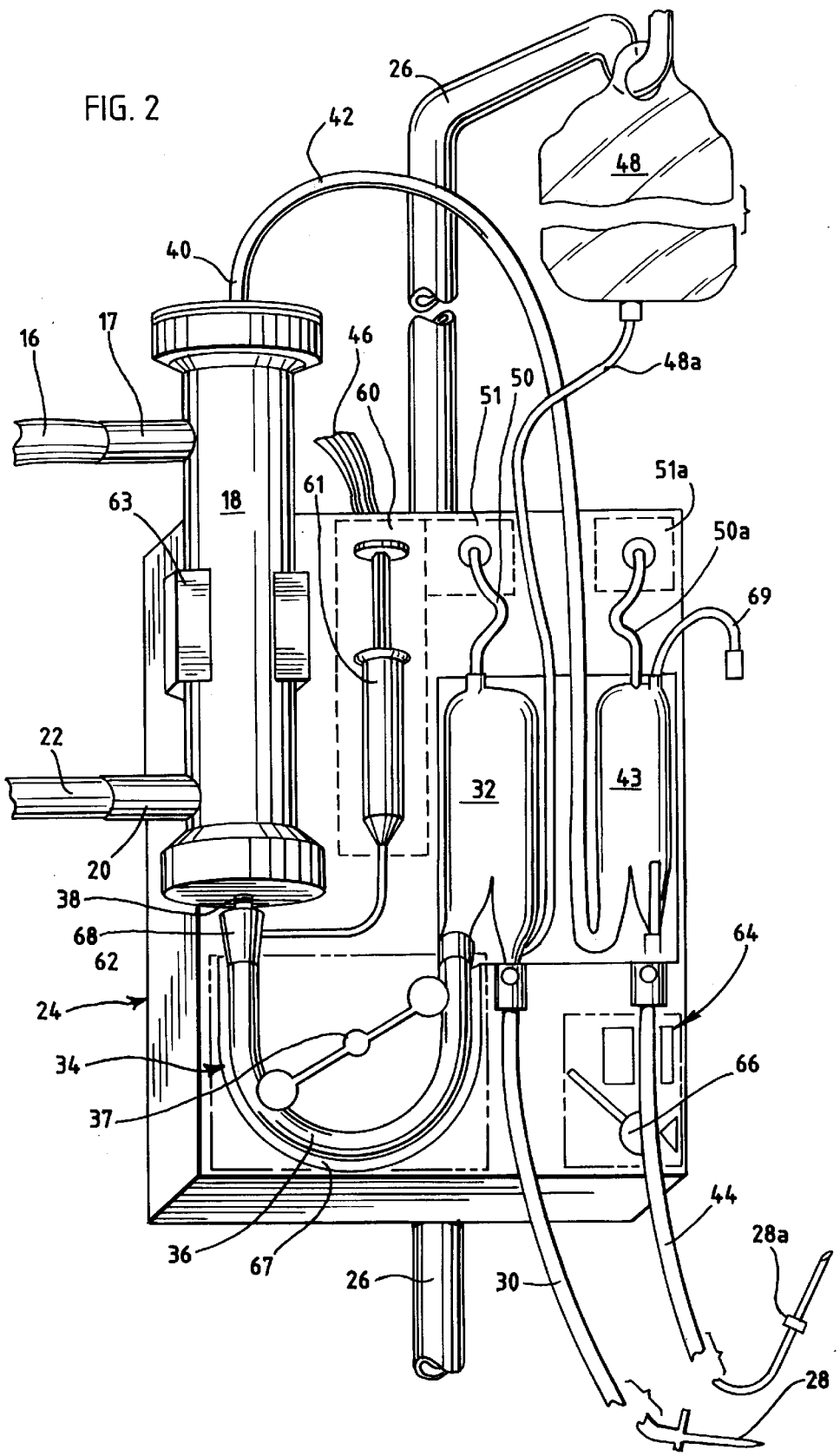

SEPARABLE HEMODIALYSIS SYSTEM

This is a continuation of U.S. application Ser. No. 08/301,765, filed Sep. 7, 1994, abandoned.

BACKGROUND OF THE INVENTION

Hemodialysis systems generally comprise a console or cabinet which provides both the blood and dialysate handling and processing functions that are necessary for hemodialysis. In prior art systems, the membrane dialyzer is mounted on the console, along with blood conduit set containing the bubble traps of the arterial and venous conduits, and the blood pump segment of the arterial conduit, which is typically of the roller pump type.

Inside of the console, the dialysate handling and processing equipment includes a proportioning system if the hemodialysis system is of the type which mixes a dialysis concentrate with water to form the dialysate. Temperature gauges, conductivity meters, a dialysis solution pump, and other known components for the processing, heating, monitoring, and pumping of dialysate through the membrane dialyzer unit are also provided in the console.

Also a pair of tubular dialysate conduits are provided for connecting the membrane dialyzer with a supply of dialysate, these dialysate conduits being fairly short since the membrane dialyzer is mounted on the face of the system console, or on a pole mounted on or near the system console.

The console also includes the blood handling and processing equipment comprising typically a blood pump, heparin pump, air bubble detector, line clamp, and blood pressure monitors and alarms. This equipment acts upon and/or communicates with the blood pathway inner lumens of the arterial and venous blood conduit sets.

The arterial and venous blood conduit sets are also connected to the membrane dialyzer, as well as being connected to the patient, to provide an extracorporeal blood flow circuit between the membrane dialyzer and the patient. Since the membrane dialyzer is carried on the console during the hemodialysis procedure, the arterial and venous blood conduit sets are typically each about eight feet long, since the relationship between the dialysis chair or bed and the hemodialysis system console is relatively fixed, and access sites on the patient range from the lower leg to the jugular vein. To avoid undue variation of the types of blood conduit sets, most or all of them provide such long tubing.

Such long tubing creates a significant extracorporeal blood volume that causes a strain on the patient's vascular system. Any reduction in extracorporeal blood volume (without an attendant rise in pressure drop) would result in a significant reduction in hypotension of other hemodynamic problems currently endemic to hemodialysis.

Also, typically, the arterial and venous blood conduit sets for hemodialysis are disposed of after one use, or a few uses at most. Thus, the cost of the sets represents a significant percentage of the cost of dialysis. Any reduction in the cost of the arterial and venous blood conduit sets would comprise a significant reduction in the cost of the long term hemodialysis of a patient, since the procedure is performed on a chronic basis, typically three times a week.

In accordance with this invention a modification of hemodialysis systems is provided, in which the length of the tubing of the arterial and venous blood conduit sets can be substantially reduced, by separating the blood processing and dialysate processing equipment into two consoles such that the blood processing equipment can be brought closer (horizontally) to the patient's vascular access, and closer (vertically) to the patient's heart level. This results in a potentially significant cost savings in the disposable sets, since more than a hundred fifty of them are typically used annually by each dialysis patient.

By way of further advantage, a reduction in the length of the tubing of the blood conduit sets reduces the priming volume of the sets, which, in turn, can reduce the loss of blood by the patient in each hemodialysis procedure. Also, at high blood flow rates, the pressures in a set with blood tubing of reduced length can have a reduced pressure drop. This reduces the risk of collapsing blood vessels in the patient, due to excessive suction pressure at the arterial end of the blood conduit set.

By way of further advantage, the pressure monitoring means (pressure transducers) can more practicably brought to the level of the patient's heart, thus eliminating blood pressure reading errors caused by differentials in the height of the patient relative to the height of the pressure monitoring means. The shortness of the tubing and the correct height of the pressure monitoring means allows very accurate blood pressure measurements in the patient's fistula or graft as called for in an ideal dialysis.

DESCRIPTION OF THE INVENTION

In accordance with this invention, a hemodialysis system is provided which comprises the following.

A dialysate handling unit is present for providing hemodialysis solution to the patient. The dialysate handling unit comprises a hemodialysis solution pump plus hemodialysis solution safety monitoring means, comprising typically conventional items such as a conductivity meter and a blood detector. Also, heating means for warming the dialysate to a desired temperature may be provided, as well as other conventional accessories such as a proportioning system for mixing concentrate with water to produce the dialysate, and providing negative pressure for delivering dialysate at subatmospheric pressures to the membrane dialyzer.

A first, flexible conduit is also provided for conveying fresh dialysate from the dialysate handling unit to the membrane dialyzer. A second flexible conduit is provided for conveying the spent dialysate away from the membrane dialyzer, either to a drain, or back to the dialysate unit for recirculation in desired circumstances, or for use in a known system for the measurement of ultrafiltration, for example.

Also, a blood handling unit is present, which comprises a membrane dialyzer holder optionally including a pole for carrying a membrane dialyzer holder, a blood pump, and means for safely handling blood as it is pumped from the patient, through the membrane dialyzer, and back to the patient. Such means for safely handling the blood may comprise any or all of a bubble detector, a heparin pump, pressure monitoring means on the arterial and venous blood conduits, line clamps, and the like in accordance with conventional practice.

In accordance with this invention, the equipment of the dialysate handling unit and the blood handling unit (together with the extra-corporeal circuit) are separate from each other and typically movable relative to each other while hemodialysis is being performed. For example, the blood handling unit may be carried on an I.V. pole next to the patient or a pole attached to the bed or chair, and positioned so that the arterial and venous blood conduits of the extra corporeal circuit each may be substantially shortened from their present, conventional eight foot lengths. Typically, the blood conduit lines used in this invention may each have a length of about one to three feet. On the other hand, the first, flexible conduit for dialysate is typically substantially lengthened over the corresponding conduit of the prior art, for example to a length of at least about six feet.

Thus, the console of the dialysate handling unit may in this invention be conveniently spaced from the patient, with the dialysate passing through a lengthened first conduit to reach the membrane dialyzer and/or the blood handling unit which carries the dialyzer.

The second conduit for conveying the spent dialysate away may also be lengthened, either to return the dialysis solution to the dialysate handling unit or to communicate with a drain, as may be desired.

Also, the dialysate handling unit may carry an electronic system for control of the system functions, with a cable communicating between the electronic system and the blood handling unit, being typically of a length similar to the first flexible conduit. Thus, the console containing the dialysate handling unit can provide power and control from its electronic system to the blood pump and any other electrically operated components of the blood handling unit, for example automatic blood flow shut off valves, the bubble detector, automatic pumps or valves for the administration of heparin or saline, and the like.

The blood pump of the blood handling unit may comprise a conventional roller pump which comprises a rotor and an approximately U-shaped track for receiving blood pump tubing. It is preferred for the U-shaped track to be in the position of a rightside up (upright) U, which facilitates the direct connection of the blood pump tubing to the membrane dialyzer unit and to a bubble trap. Such an arrangement is taught in Utterberg U.S. patent application Ser. No. 07/254,028 filed Jun. 6, 1994 and entitled "Blood Air Trap Chamber", U.S. Pat. No. 5,520,640. Significant advantages are achieved in a system of this type that makes use of a roller pump, where the U-shaped track of the blood tubing is upright.

Thus, by this invention it becomes possible to shorten the tubing in the blood conduit sets for hemodialysis. Since the blood conduit sets are regularly replaced in this chronic and frequent procedure, any small saving in the cost of the set rapidly multiplies itself over a period of time. Also, a reduction in the priming volume and the pressure drop of the blood conduit sets provides significant functional advantages in the hemodialysis procedure. These advantages are achieved by separating the dialysate handling unit and the blood handling unit (as defined above), and connecting them with a lengthened, first, flexible inlet conduit for dialysate. One also typically provides a lengthened electronic cable for power and control of the blood handling unit from the dialysate handling unit and a lengthened, second, flexible outlet conduit for dialysate.

The first and second hemodialysis solution conduits and the electronic cable are reusable parts which can be reused for hundreds of dialysis procedures. Thus, the slightly increased cost of the increased length of these items is basically negligible, compared with the cost savings provided by the shortened blood sets, as accomplished in accordance with this invention.

Also, it is preferred for the hemodialysis system of this invention to use a membrane dialyzer, preferably a hollow fiber dialyzer, and which is mounted in the blood handling unit with the blood outlet of the membrane dialyzer being positioned higher than the blood inlet. This corresponds to a conventional "priming" position of a hollow fiber hemodialyzer in which air bubbles move upwardly through the blood outlet. Then, in the prior art, after priming of at least the blood conduit, the dialyzer is inverted by about 180° so that the blood outlet is vertically lower than the blood inlet. This is another reason that the blood lines between the patient and the blood handling units of the prior art have to be longer than in this present invention. By this invention, one can proceed with dialysis without inverting or "flipping" the dialyzer.

One reason this is possible is that, in traditional dialysis machines, the degassing of the incoming water and/or dialysate was not very good, so that under the significant negative pressure that was required for adequate ultrafiltration, dissolved air would out-gas in the dialysate in the form of bubbles. The typical membrane dialyzer is in the blood outlet end-down position during operation so the dialysate air bubbles may rise to the top of the dialyzer in the dialysate flow path since typical membrane blood and dialysis flows are countercurrent. That is, with the blood outlet in the end-down position of dialysis, the dialysate outlet is vertically higher than the dialysate inlet. The dialysate bubbles, thus can rise and exit the dialysate outlet (which is at blood inlet end of the membrane or dialyzer). If the membrane dialyzer were run with the dialysate outlet end down (i.e., the priming position) with traditional dialysis machines. The dialysate air bubbles would accumulate in the dialysate compartment of the membrane dialysate, "masking" the membrane. This will reduce the performance of the membrane dialyzer. However, with new high flux dialysis membranes, ultrafiltration takes place at significantly lower negative pressures, so there is less tendency for air to outgas into bubbles in the dialysate during operation. Also, modern dialysis machines have much better gas removing capability from the incoming water and/or dialysate, all of which basically reduces or eliminates the air bubble problem in dialysate. However, on the blood side, there is typically an increased blood flow rate in modern, state of the art dialysis, which means that in the pre-pump segments of the arterial blood conduit line, it is the blood that is seeing much higher negative pressure. Blood has a higher degree or dissolved gas in it. Thus, gas bubbles may come out in the blood as the higher flows "stretch" the blood coming through the narrow constriction of the blood access device, typically a 14–17 gauge fistula needle. There is an added advantage, therefore, in having the blood flow upwardly during dialysis, which is also the priming position, so that there is no necessity or advantage in rotating the dialyzer by 180° for operation after priming. However, this has not been recognized in the prior art, and rotation of the hollow fiber dialyzer between priming and operation is still normally followed in the prior art.

Thus, by this invention, the blood lines can be so short that inverting of the dialyzer after priming is impossible and not needed without encountering disadvantage.

DESCRIPTION OF THE DRAWINGS

FIG. 2 is an enlarged,perspective view of a preferred blood handling unit as shown in FIG. 1.

DESCRIPTION OF SPECIFIC EMBODIMENTS

Figure 1:
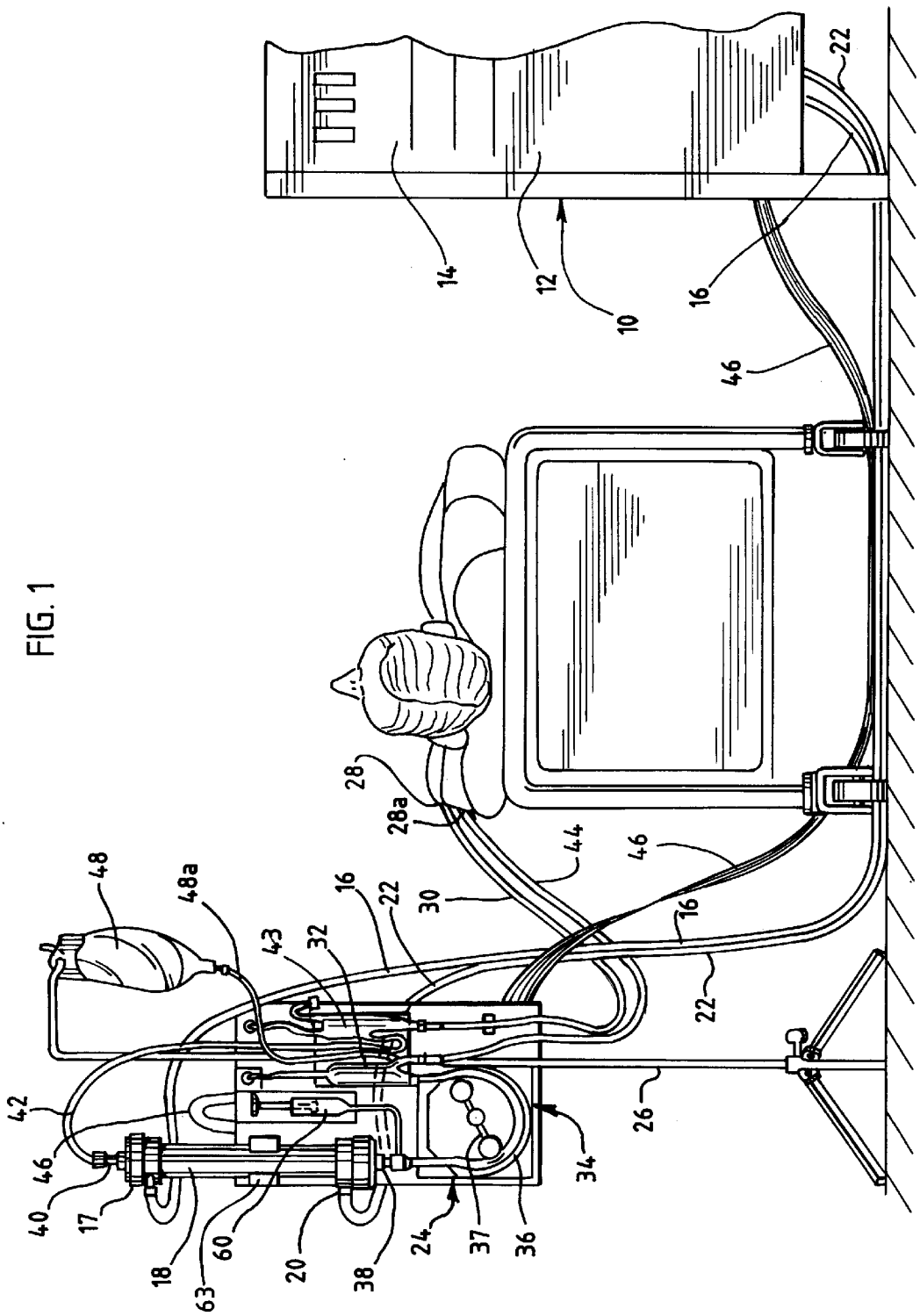
FIG. 1 is a perspective view of a hemodialysis system in accordance with this invention, in the process of use.

Referring to the drawings, a hemodialysis system is shown which comprises a dialysate handling unit 10 having an outer console 12, which contains a conventional solution pump, a dialysate proportioning system, and various hemodialysis solution safety monitoring mechanisms such as a conductivity meter, a blood detector, and other conventional items for the preparation, monitoring, and delivery of hemodialysis solution to a membrane dialyzer. Additionally, a heater for the dialysate may be provided, as well as a temperature control device, all of which are basically conventional, there being numerous dialysis machines which are currently available for clinical use. A control panel 14 is provided on the console for control of the various dialysis functions, including the functions that relate to the safe handling of blood as it is pumped from the patient through a membrane dialyzer 18 and back to the patient. Additionally, a conventional degassing mechanism may be provided within console 12 as well. Alternatively, blood monitoring can happen on the blood handling unit described below.

A first, flexible conduit 16 communicates from the hemodialysis solution unit 10 to the dialysate inlet 17 of membrane dialyzer 18, which is specifically shown to be of the hollow fiber type. The membrane dialyzer preferably is mounted on the blood handling unit 24 by means of a clamp 63 or the like. Alternatively, the membrane dialyzer can be mounted on the I.V. pole by a similar clamp.

The dialysate enters dialyzer 18 at port 17, flowing between the hollow fibers in countercurrent relation to flowing blood within the hollow fibers, and then out of port 20 into second, flexible conduit 22. In this embodiment, second flexible conduit 22 returns spent dialysate to the dialysate handling unit 10 for the measuring of ultrafiltration in a conventional manner. However, if desired, second, flexible conduit 22 may simply lead to a drain.

The blood handling unit 24 is small enough to be carried on a conventional I.V. pole 26, which may be moved during the dialysis procedure while carrying blood handling unit 24 to be close to the patient. Unit 24 may be placed by the patient's shoulder if the blood access site is in the arm or jugular vein, or by his feet if the blood access site is in the lower leg. Blood handling unit 24 can be moved to accomplish this, while the larger dialysate unit 10 remains stationary and relatively distant from the patient. The blood handling unit will comprise a blood pump module 34, blood pressure monitoring modules 51, 51a, bubble detector module 64, blood line clamp 66, and preferably a heparin pump module 60 and dialyzer holder 63.

Blood access needle connectors 28 and 28a are shown to be connected to conventional single lumen fistula needles, but which may also be any other conventional sources of blood access. For example, one double lumen needle may be used. Arterial conduit tubing is provided which comprises tubing 30, which communicates with a bubble trap chamber 32 similar to that described in the previously cited Utterberg patent application. The blood passes from arterial conduit tubing 30 to bubble trap chamber 32, and from there to a conventional roller pump 34. Roller pump tubing 36 extends from chamber 32 through a U-shaped track 67 surrounding rotor 37 of roller pump 34, in which the U-shape of the track is in upright form, for advantages described in the previously described Utterberg application.

Blood is thus pumped from chamber 32, through the roller pump around U-shaped track 36, to preferably a combination dialyzer/pump segment connector 68, to the blood inlet or arterial entrance 38 of hollow fiber dialyzer 18. Blood passes through the hollow fibers upwardly through membrane dialyzer 18, to exit through the blood outlet (venous port) 40 of the membrane dialyzer into a length of blood tubing 42, which communicates with bubble trap chamber 43, which is preferably defined with chamber 32 in an integral structure, as disclosed in the previously cited application. The blood passes through chamber 43 and out the bottom through venous conduit tubing 44, back to needle connector 28a for readministration to the patient.

A multiple wire electronic cable 46 communicates between hemodialysis solution unit 10 and blood dialysis unit 24, to provide power and/or electronic control to blood pump 34 and any other electrically powered components of blood dialysis unit 24 such as pressure monitor 51 and 51a and a bubble detector 64, and a line clamp 66, which are generally all of conventional design except as otherwise shown. The various electrically powered systems of blood dialysis unit 24 may be controlled by a conventional electronic system of the hemodialysis solution unit 10, with appropriate controlling signals being sent through cable 46 in both directions.

A saline solution bag 48 is provided in conventional manner to communicate via line 48a with chamber 32. Lines and connectors 50, 50a may be used in conventional manner to connect chambers 32, 43 to pressure monitors 51 and 51a. A heparin pump 60 may be included in blood dialyzer unit 24 and administered in conventional manner via syringe 61 through a branch connector line 62 which may be placed as desired in the system.

Tubing 69 provides syringe or needle access to the system.

In this specific embodiment, blood tubing 30, 44 may each have a length respectively of about one to three feet between needle connectors 28, 28a and bubble traps 32, 43. Blood tubing 42 is likewise of a length on the order of one foot. Thus, there is a substantial shortening of the blood tubing in the system disclosed, when compared with the use of corresponding and conventional arterial and venous blood conduit sets, each of which can have approximately a eight foot length of blood tubing analogous to tubings 30 or 44. It can be thus seen that by this invention a savings of more than fifty percent in the blood tubing lines can be achieved, resulting in a proportionate reduction in priming volume and pressure resistance to flow.

Flexible dialysate conduits 16, 22 may be on the order of six to fifteen feet in length, or whatever length is desirable so that the I.V. pole 26 can be placed close to the patient so that the short blood tubings 30, 44 are adequate. Blood handling unit 24 is thus substantially spaced from solution handling unit 10, which may be conveniently placed in a more remote location, out of the way of the technicians in the area. Similarly, electronic cable 46 may be of a corresponding length on the order of six to fifteen feet.

Thus, by this invention, hemodialysis may proceed in a manner which is substantially identical to currently available membrane hemodialysis procedures. However, the functions of the hemodialysis system that pertain to the safe handling and pumping of the blood from the patient, through the membrane dialyzer, and back to the patient are physically separated from the functions of the hemodialysis system which pertain to the providing of dialysate to the patient, including if desired the preparation thereof. This permits the shortening of the lengths of the blood tubing, which has both functional and economic advantages, typically with a corresponding lengthening of the dialysis solution flexible conduits and the control cable between the two units 10, 24. This latter modification is of relatively low cost because the latter components are reusable on a long term basis. Also, dialyzer 18 may be primed and then used without inverting the dialyzer, with blood inlet 38 being typically lower than blood outlet 40.

The above has been offered for illustrative purposes only, and is not intended to limit the scope of the invention of this application, which is as defined in the claims below.

That which is claimed is:

1. A hemodialysis system which comprises:

a dialysate handling unit for providing hemodialysis solution to the patient, comprising a hemodialysis solution pump and a hemodialysis solution safety monitoring apparatus;

a blood handling unit which comprises a membrane dialyzer holder, a blood pump, and equipment for safely handling blood as it is pumped from the patient, through a membrane dialyzer and back to the patient, said blood handling unit being carried on a moveable stand, separate and spaced from said dialysate handling unit;

a first conduit for conveying fresh dialysate from said dialysate handling unit to a membrane dialyzer in the blood handling unit, and a second conduit for conveying spent hemodialysis solution away from said blood handling unit;

said dialysate handling unit and said blood handling unit being movably separate from each other and free of any mechanical connection preventing them from being moveable in all directions relative to each other while hemodialysis is being performed, the dialysate handling unit being free of blood-contacting components and the blood handling unit being free of dialysis solution processing components other than said membrane dialyzer, said blood handling unit being positioned closer to a patient treatment site than to said dialyzate handling unit.

2. The hemodialysis system of claim 1 in which said dialysate handling unit also comprises a proportioning system.

3. The hemodialysis system of claim 1 in which said blood handling unit also comprises a blood conduit connected through said blood pump and membrane dialyzer and which has at least one bubble trap in said blood conduit.

4. The hemodialysis system of claim 3 in which the portion of said blood conduit extending from said bubble trap to the patient is shorter than the first conduit.

5. The hemodialysis system of claim 4 in which said blood conduit portion has a length of about 1 to 3 feet, and the first conduit has a length of at least about 6 feet.

6. The hemodialysis system of claim 1 in which a membrane dialyzer is carried in said dialyzer holder, and said equipment for safely handling blood comprises a pair of blood lines each communicating between patient connecting access devices and said membrane dialyzer, said blood lines each being of less length than the first conduit.

7. The hemodialysis system of claim 1 in which said dialysate handling unit carries an electronic system for control of all system functions, and a cable communicating between said electronic system and said blood handling unit to provide power and control from said electronic system to the blood pump and any other electrically operated components of said blood handling unit.

8. The hemodialysis system of claim 1 in which said blood handling unit further comprises an electronic bubble detector.

9. The hemodialysis system of claim 1 in which said second conduit connects with said dialysate handling unit.

10. The hemodialysis system of claim 1 in which said blood pump comprises a rotor and a U-shaped track for receiving blood tubing which is part of said equipment for safely handling blood, said U-shaped track being in the form of an upright U.

11. The hemodialysis system of claim 1 in which a dialyzer having a blood inlet and outlet is mounted in the remainder of the blood handling unit with said blood outlet positioned higher than said blood inlet, the dialyzer being connected to blood lines so short that the dialyzer cannot be inverted after priming to dialyze in that inverted position.

12. A hemodialysis system which comprises:

a dialysate handling unit for providing dialysate to a patient, comprising a hemodialysis solution pump and hemodialysis solution safety monitoring apparatus;

a blood handling unit which comprises a membrane dialyzer holder carrying a membrane dialyzer, a blood pump, and equipment for safely handling blood as it is pumped from the patient, through a membrane dialyzer in the holder, and back to the patient, said blood pump comprising a rotor and a U-shaped track containing a portion of blood tubing as part of said equipment for safely handling blood, said U-shaped track being in a form of an upright U, one end of the blood tubing in said U-shaped track connecting directly to said membrane dialyzer, the other end of the blood tubing in said track being directly connected to a bubble trap, said bubble trap being also connected to a blood conduit which communicates with a connector for an access device to the patient, said blood handling unit being carried on a moveable stand, separate and spaced from said dialysate handling unit;

a first conduit for conveying fresh dialysate from said dialysate handling unit to a membrane dialyzer in the blood handling unit, and a second conduit for conveying spent dialysate away from the blood handling unit; said dialysate handling unit and the blood handling unit being movably separate from each other and free of any mechanical connection preventing them from being moveable in all directions relative to each other while hemodialysis is being performed, the dialysate handling unit being free of blood-contacting components and the blood handling unit being free of dialysate solution processing components other than the membrane dialyzer, said blood conduit being shorter than said first conduit, said blood handling unit being positioned closer to a patient treatment site than to said dialyzate handling unit.

13. The hemodialysis system of claim 12 in which a pair of said blood conduits are present, each blood conduit having a length of about 1 to 3 feet, and the first conduit has a length of at least about 6 feet.

14. The hemodialysis system of claim 13 in which said membrane dialyzer has a blood inlet and outlet, and is mounted in the remainder of the blood handling unit with said blood outlet positioned higher than said blood inlet, the dialyzer being connected to blood lines so short that the dialyzer cannot be inverted after priming to dialyze while inverted.

15. The hemodialysis system of claim 12 in which said dialysate handling unit carries an electronic system for control of system functions, a cable communicating between said electronic system and said blood handling unit to provide power and control from said electronic system to the blood pump.

16. The hemodialysis system of claim 15 in which said blood handling unit further comprises a length of tubing; means at one end of the tubing for connection with a blood access device; and a bubble trap connected to the other end of said length of tubing, said length of tubing being from 1 to 3 feet in length.

17. A hemodialysis system which comprises:

a dialysate handling unit for providing hemodialysis solution to the patient, comprising a hemodialysis solution pump and hemodialysis solution safety monitoring equipment;

a blood handling unit which comprises a membrane dialyzer holder, a blood pump, and equipment for safely handling blood as it is pumped from the patient, through a membrane dialyzer, and back to the patient, said blood handling unit being carried on a moveable stand, separate and spaced from said dialysate handling unit;

a first conduit for conveying fresh dialysate from said dialysate handling unit to a membrane dialyzer in the blood handling unit, and a second conduit for conveying spent hemodialysis solution away from said blood handling unit;

said dialysate handling unit and said blood handling unit being movably separate from each other and free from any mechanical connection preventing them from being moveable in all directions relative to each other while hemodialysis is being performed, said dialysate handling unit carrying an electronic system for powering and controlling all system functions of blood handling and dialysate handling, and a cable communicating between said electronic system and said blood handling unit to provide power and control from said electronic system to the blood pump and any other electrically operated components of said blood handling unit, said blood handling unit being positioned closer to a patient treatment site than to said dialyzate handling unit.

18. The hemodialysis system of claim 17 in which said blood handling unit also comprises a blood conduit connected through said pump and membrane dialyzer and which has at least one bubble trap in said blood conduit, the portion of the said blood conduit extending from said bubble trap to the patient being shorter than the first conduit.

19. The hemodialysis system of claim 18 in which said blood handling unit further comprises an electronic bubble detector and in which said second conduit connects with said dialysate handling unit.

20. The hemodialysis system of claim 19 in which said blood pump comprises a rotor and a U-shaped track for receiving blood tubing which is part of said equipment for safely handling blood, said U-shaped track being in the form of an upright U.

21. The hemodialysis system of claim 20 in which a dialyzer having a blood inlet and outlet is mounted in the remainder of the blood handling unit with said blood outlet positioned higher than said blood inlet, the dialyzer being connected to blood lines so short that the dialyzer cannot be inverted after priming to dialyze in that inverted position.

22. A hemodialysis system which comprises:

a dialyzate handling unit for providing hemodialysis solution to the patient;

a blood handling unit which comprises a membrane dialyzer holder and equipment for safely handling blood as it passes from the patient, through a membrane dialyzer, and back to the patient, said blood handling unit being carried on a movable stand, separate from said dialyzate handling unit;

a first conduit for conveying fresh dialyzate from said dialyzate handling unit to a membrane dialyzer in the blood handling unit, and a second conduit for conveying spent hemodialysis solution away from said blood handling unit;

said dialyzate handling unit and said blood handling unit being spaced and movably separate from each other and free of any mechanical connection preventing them from being movable in all directions relative to each other while hemodialysis is being performed, the dialyzate handling unit being free of blood-contacting components and the blood handling unit being free of dialysis solution processing components other than said membrane dialyzer.

23. The hemodialysis system of claim 22 in which a blood conduit is connected to said membrane dialyzer, which blood conduit has at least one bubble trap in the blood conduit, and in which the portion of said blood conduit extending from said bubble trap to the patient is shorter than the first conduit.

24. The hemodialysis system of claim 23 in which said blood conduit portion has a length of about 1 to 3 feet and the first conduit has a length of at least about 6 feet.

25. The hemodialysis system of claim 22 in which said blood pump comprises a rotor and a U-shaped track for receiving blood tubing which is part of said equipment for safely handling blood, said U-shaped track being in the form of an upright U.

26. The hemodialysis system of claim 22 in which blood conduits are carried by said blood handling unit for communication between the blood handling unit and said patient for inflow and outflow of blood to and from said patient, each blood conduit being shorter than said first conduit.

27. The hemodialysis system of claim 26 in which said blood handling unit is positioned closer to a patient treatment site than to said dialyzate handling unit.

\* \* \* \* \*